(12) United States Patent
Larsen

(10) Patent No.: US 11,357,926 B2
(45) Date of Patent: Jun. 14, 2022

(54) DRUG DELIVERY DEVICE WITH SOUND TRANSDUCER

(71) Applicant: Novo Nordisk A/S, Bagsvaerd (DK)

(72) Inventor: Andre Larsen, Dragoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 190 days.

(21) Appl. No.: 16/611,578

(22) PCT Filed: May 4, 2018

(86) PCT No.: PCT/EP2018/061541
§ 371 (c)(1),
(2) Date: Nov. 7, 2019

(87) PCT Pub. No.: WO2018/206442
PCT Pub. Date: Nov. 15, 2018

(65) Prior Publication Data
US 2020/0197615 A1   Jun. 25, 2020

(30) Foreign Application Priority Data

May 9, 2017 (EP) ...................................... 17170126

(51) Int. Cl.
*A61M 5/315* (2006.01)
*A61M 5/24* (2006.01)
(Continued)

(52) U.S. Cl.
CPC ............ *A61M 5/3157* (2013.01); *A61M 5/24* (2013.01); *A61M 5/31568* (2013.01);
(Continued)

(58) Field of Classification Search
CPC .. A61M 5/3157; A61M 5/24; A61M 5/31568; A61M 5/5086; A61M 5/2033; A61M 2005/3126
See application file for complete search history.

(56) References Cited

U.S. PATENT DOCUMENTS 5,620,004 A * 4/1997 Johansen ............... A61B 7/003
600/529
2009/0306633 A1   12/2009 Trovato et al.
(Continued)

FOREIGN PATENT DOCUMENTS

CN   203303452 U   11/2013
JP   S50155889 U   12/1975
(Continued)

*Primary Examiner* — Nathan R Price
*Assistant Examiner* — Tasnim Mehjabin Ahmed
(74) *Attorney, Agent, or Firm* — Wesley Nicolas

(57) ABSTRACT

A drug delivery device is provided comprising a drug-filled cartridge or means for receiving a drug-filled cartridge, and drug expelling means comprising expelling means for expelling an amount of drug from the cartridge, and an indicator member arranged to move corresponding to an action performed on or by the drug delivery device. The device further comprises an energy source, wireless communication means, sensor means adapted to detect movement of the indicator member, and a processor adapted to (i) receive input from the drug delivery device indicative of indicator member movement and (ii) control the communication means to transmit a data signal comprising coded information derived from received input from the sensor means, wherein the wireless communication means is in the form of a sound transducer.

11 Claims, 8 Drawing Sheets

(51) Int. Cl.
  *A61M 5/31*   (2006.01)
  *A61M 5/50*   (2006.01)
  *A61M 5/20*   (2006.01)

(52) U.S. Cl.
  CPC ......... *A61M 5/5086* (2013.01); *A61M 5/2033* (2013.01); *A61M 2005/3126* (2013.01); *A61M 2205/3561* (2013.01); *A61M 2205/505* (2013.01); *A61M 2205/581* (2013.01); *A61M 2205/8206* (2013.01)

(56) References Cited

U.S. PATENT DOCUMENTS

| | | | |
|---|---|---|---|
| 2009/0318865 | A1 | 12/2009 | Moller et al. |
| 2011/0190693 | A1 | 8/2011 | Takatsuka et al. |
| 2013/0310756 | A1* | 11/2013 | Whalley ............. A61M 5/3129 604/189 |
| 2015/0290396 | A1 | 10/2015 | Nagar et al. |
| 2016/0000998 | A1 | 1/2016 | Estes |
| 2016/0166766 | A1 | 6/2016 | Schuster et al. |
| 2016/0259913 | A1 | 9/2016 | Yu et al. |
| 2016/0263327 | A1* | 9/2016 | Radmer ................ G16H 20/17 |
| 2017/0007765 | A1* | 1/2017 | Cowe ................ A61M 5/2033 |
| 2021/0077736 | A1* | 3/2021 | Larsen ................ A61M 5/3157 |

FOREIGN PATENT DOCUMENTS

| | | | | |
|---|---|---|---|---|
| JP | 2011156005 | A | 8/2011 | |
| WO | 2010052275 | A2 | 5/2010 | |
| WO | 2015071354 | A1 | 5/2015 | |
| WO | WO-2015071354 | A1 * | 5/2015 | .......... A61M 5/3158 |
| WO | 2015185687 | A1 | 12/2015 | |

* cited by examiner

DRUG DELIVERY DEVICE WITH SOUND TRANSDUCER

CROSS-REFERENCE TO RELATED APPLICATIONS

This application is a 35 U.S.C. § 371 National Stage application of International Application PCT/EP2018/061541 (published as WO 2018/206442), filed May 4, 2018, which claims priority to European Patent Application 17170126.1, filed May 9, 2017, the contents of all above-named applications are incorporated herein by reference.

The present invention generally relates to medical devices comprising monitoring means configured to capture information relating to an expelled dose of drug. In a specific aspect the invention relates to communication means allowing captured data to be transmitted to an external device in a cost-effective way.

BACKGROUND OF THE INVENTION

In the disclosure of the present invention reference is mostly made to drug delivery devices comprising a threaded piston rod, such devices being used e.g. in the treatment of diabetes by subcutaneous delivery of insulin, however, this is only an exemplary use of the present invention which with corresponding advantages may be used for other drugs and other types of drug delivery devices.

Subcutaneous drug delivery devices have greatly improved the lives of patients who must self-administer drugs and biological agents. Such drug delivery devices may take many forms, including "durable" devices adapted to be used with pre-filled cartridges for an extended period of time, e.g. a number of years, and prefilled "disposable" devices adapted to be discarded when having been emptied. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in conventional electronic data acquisition functionality in the device it-self. Addressing this problem WO 2015/071354 discloses a prefilled drug delivery device of the pen-type provided with an "electronic label" mounted on the outer surface of the pen device and adapted to detect a dosing event and display a corresponding parameter, e.g. time and/or dose amount. To cost-effectively provide a "label-like" electronic assembly one or more or all of the detection means, display, processor, and energy source may be in the form of printed electronics. An antenna may also be formed on the flexible sheet by printing, the processor being adapted to transmit data to an external receiver via the antenna.

For the purpose of providing audible alerts or messages to the user, US 2013/0310756, US 2017/0007765 and US 2016/0000998 disclose medical devices provided with a loudspeaker. US 2009/0306633 discloses an implantable capsule which may communicate with an external controller via ultrasound allowing adequate transmission through the patient's body.

Having regard to the above, it is an object of the present invention to provide a drug delivery with the ability to capture dose related data and transmit data to an external device for subsequent analysis, storage and/or display, yet allowing the functionality to be cost-effectively incorporated in a pre-filled and thus disposable device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device is provided, comprising a housing having an exterior surface, a drug-filled cartridge or means for receiving a drug-filled cartridge, the cartridge comprising an outlet and an axially displaceable piston, drug expelling means comprising a drive member adapted to engage and axially move the piston to thereby expel an amount of drug from the cartridge through the outlet, and an indicator member arranged to move corresponding to an action performed on or by the drug delivery device. The drug delivery device further comprises electronic circuitry comprising sensor means adapted to detect movement of the indicator member, wireless communication means, a processor adapted to (i) receive input from the sensor means indicative of indicator member movement and (ii) control the wireless communication means to transmit a coded signal comprising information derived from received input from the sensor means, as well as an energy source for powering the components of the electronic circuitry. Corresponding to the first aspect of the invention the wireless communication means is in the form of a sound transducer. The controller is adapted to create a data signal coded using a given protocol allowing a corresponding receiver device to de-code the signal and retrieve the contained information.

By this arrangement a drug delivery device is provided which cost- and energy-effectively allows the device to communicate with an external device comprising a corresponding sound transducer, e.g. in the form of a smartphone, the build-in microphone being used as a sound transducer.

The sound transducer may be a sound emitter allowing data to be transmitted to the external device, or the sound transducer may be a sound receiver allowing data to be transmitted to the drug delivery device. In an exemplary embodiment the device comprises both a sound transmitter and a sound receiver, which may be in the form of a single bidirectional sound transducer. The sound transducer may emit sound signals in the near-ultrasound/ultrasound frequency range, e.g. in the 15-25 kHz range and may be in the form of a piezoelectric sound transducer.

In an exemplary embodiment the drug delivery device comprises a flexible carrier foil (or sheet) on which is formed or mounted the energy source, the sound transducer, and the processor, the flexible carrier foil being mounted on the exterior surface of the housing. In this way a subassembly for the drug delivery device is provided in the form of an electronic label device. The definition that the sound transducer is "formed on" the flexible foil covers the situations in which a portion of the flexible foil at least partially forms the sound transducer. For example, the flexible carrier foil may be a piezoelectric foil, a portion of the piezoelectric foil forming the sound transducer. To cost-effectively provide a "label-like" electronic assembly one or more or all of the detection means, display, processor, and energy source may be in the form of printed electronics.

In a further exemplary embodiment the housing exterior surface comprises a cavity over which at least a portion of the piezoelectric foil is arranged. Alternatively the housing comprises a portion with reduced wall thickness over which at least a portion of the sound transducer is arranged. In this way a sound emitting transducer serves as a driver for the housing membrane portion to which it is attached.

The drug delivery device may comprise a display, the processor being adapted to, based on input from the input means, control the display to display a time parameter related to the time the input means was actuated and/or the amount of drug expelled from the drug delivery device during an expelling event.

In exemplary embodiments the drug expelling means further comprises a dose setting member allowing a user to set a dose amount of drug to be expelled, the indicator element being adapted to move during setting and/or expelling of a dose amount, the amount of movement being indicative of the size of the set and/or expelled dose amount.

In a simplified version only a simple movement is detected, e.g. an axial or a rotational movement of the indicator member, this being indicative of a dosing event taking place.

The electronic circuitry may comprise a memory allowing a data log to be created, this allowing data to be stored for subsequent transmission.

The drug delivery device may be prefilled comprising a permanently mounted drug-filled cartridge which cannot be removed without damage to the device.

In a second aspect of the invention an electronic label adapted to be mounted on an exterior surface of a drug delivery device housing is provided, the drug delivery device comprising a housing having an exterior surface, a drug-filled cartridge or means for receiving a drug-filled cartridge, the cartridge comprising an outlet and an axially displaceable piston, as well as drug expelling means comprising a drive member adapted to engage and axially move the piston to thereby expel an amount of drug from the cartridge through the outlet, and an indicator member arranged to move corresponding to an action performed on or by the drug delivery device. The electronic label comprises a flexible carrier foil (or sheet) on which are formed or mounted an energy source, a sound transducer, and a processor adapted to (i) receive input from the drug delivery device indicative of indicator member movement, and (ii) control the sound transducer.

By the above arrangements a very simple and inexpensive electronic system is provided which cost-effectively can be mounted on a drug delivery device, the low cost allowing it to be utilized on a pre-filled disposable drug delivery device. To cost-effectively provide a "label-like" electronic assembly one or more or all of the detection means, display, processor, and energy source may be in the form of printed electronics. Indeed, the electronic system could also be incorporated in a durable device.

The sound transducer may be a sound emitter allowing data to be transmitted to the external device, or the sound transducer may be a sound receiver allowing data to be transmitted to the drug delivery device. In an exemplary embodiment the label device comprises both a sound transmitter and a sound receiver, which may be in the form of a single bidirectional sound transducer. The sound transducer may emit sound signals in the 15-25 kHz range and may be in the form of a piezoelectric sound transducer.

In an exemplary embodiment the label device comprises a flexible carrier foil on which is formed or mounted the energy source, the sound transducer, and the processor, the flexible carrier foil being mounted on the exterior surface of the housing. The definition that the sound transducer is "formed on" the flexible foil covers the situations in which a portion of the flexible foil at least partially forms the sound transducer. For example, the flexible carrier foil may be a piezoelectric foil, a portion of the piezoelectric foil forming the sound transducer. The label device may be adapted to be mounted on the drug delivery device by adhesive means, and may comprise a display as described above.

The label device may comprise an upper sealing foil and a lower sealing foil bonded circumferentially to each other as well as to the upper respectively lower surface of the carrier foil and to those structures mounted or formed thereon. In this way a sealed space can be formed between the two sealing foil providing a desired low level of water permeability. This said, the carrier foil may be exposed corresponding to a portion thereof forming a sound transducer.

Alternatively the label device comprises an upper sealing foil bonded to the upper surface of the carrier foil and to those structures mounted or formed thereon. This said, the carrier foil may be exposed corresponding to a portion thereof forming a sound transducer. The lower surface of the label device may be provided with an adhesive layer and a thereto attached peelable temporary backing foil which can be removed just prior to mounting of the label device on a drug delivery device. In this way the sealing functionality of the deleted lower sealing foil can be provided by the structure on which the label device is mounted, e.g. the portion of the drug delivery device housing the label device is intended to be mounted on.

Irrespective of the design of the label device, the actual desired level of impermeability to water will be determined by the properties of the structures and components mounted or formed on the carrier foil as well as the conditions and environment the label device will be used in.

In addition to the above-described components, the label device is provided with input means which may be formed or mounted on the flexible carrier foil, the input means being adapted to be actuated, directly or indirectly, by movement of the indicator member. The input means may be in the form of galvanic contacts and/or contact-less based on e.g. induction or sound.

The input means may be in the form of a switch structure adapted to be actuated between a first and a second state. The switch structure may e.g. comprise a number of stationary contact areas formed or mounted on a contact area of the flexible sheet, the drug delivery device further comprising a moveable switch structure adapted to engage the stationary contact areas to thereby actuate the input means, the moveable switch structure being adapted to be moved by the indicator member. The moveable switch structure may be formed integrally with the flexible sheet, the moveable switch structure comprising a contact area, wherein the contact area is arranged in its operational position by bending of the flexible sheet. In the present context the term "bending" should be understood broadly including e.g. folding, turning, rotating.

Alternatively the drug delivery device may comprise one or more switch members arranged corresponding to an opening formed in the housing, at least one switch member being a moveable switch member projecting into the opening and being adapted to be moved by the indicator member, whereby the one or more switch members form a switch assembly adapted to be actuated between a first and a second state. The switch assembly may be preassembled or formed from switch members mounted individually. The flexible sheet is mounted to cover the opening and comprises contact means (terminals) adapted to engage corresponding terminals on the switch assembly to thereby provide the input means.

In an exemplary embodiment the indicator member is adapted to rotate from a set position corresponding to a set dose amount and to an end-of-dose position in which the set dose has been expelled, the input means being actuated when the indicator member has reached the end-of-dose position. During rotation of the indicator member the input means may be actuated more than once. If provided with a display, the processor may be adapted to control the display to display (i) a time parameter indicating the time when the input means was actuated, e.g. using the HH:MM format, or (ii) a time parameter indicating the time since input means was actuated, e.g. a dynamic timer using the HH:MM format or a simple version using segments for e.g. each hour.

The indicator member may have a first axial position when the drug expelling means is in a dose setting state, and a second axial position when the drug expelling means is in an expelling state, the input means being adapted to be actuated by the indicator member with the indicator member only in the second axial position.

In a further exemplary embodiment the indicator member is adapted to move from an initial position to a set position when a dose is being set, the input means being actuated when the indicator member is moved away from the initial position. As above, the processor may be adapted to control a display to display a time parameter indicating the time when input means was actuated, or a time parameter indicating the time since input means was actuated.

In a yet further exemplary embodiment, one or more flexible members provided with contact means may be bonded to the flexible sheet to provide a composite switch structure. Depending on the design and the assembly process for the drug delivery device as well as the switch design a composite switch structure may be the most cost-effective. For example, a switch structure may be mounted inside or outside the device during assembly, the flexible sheet being mounted on an external surface of the device such that contact is established between the two structures. The input means may comprise more than one switch, the switches being of the same or different designs.

In a yet further exemplary embodiment the amount of rotation of the indicator means corresponds to the amount of drug expelled from a reservoir by the expelling means, the input means being adapted to be actuated corresponding to the amount of rotation of the indicator means. If a display is provided, the processor is adapted to (i) based on input from the input means calculate the amount of drug expelled corresponding to the amount of rotation, and (ii) control the display to display the calculated amount. In addition time information related to the calculated drug amount may be display. The processor is adapted to create a dose log comprising dose amounts and associated time values. If no display is provided the processor may be adapted to transmit data in a simple "as-detected" form which then can be processed in a receiving device, e.g. a smartphone.

Alternatively the amount of rotation of the indicator means corresponds to a user-set amount of drug to be expelled from a reservoir by the expelling means, the input means being adapted to be actuated corresponding to the amount of rotation of the indicator means, and the processor is adapted to (i) based on input from the input means calculate the set amount of drug to be expelled corresponding to the amount of rotation, and, if provided, (ii) control the display to display the calculated amount. For such a design it would be possible to use the electronic display instead of a mechanical display, e.g. as on a traditional dose drum, this allowing e.g. larger numerals to be used.

The indicator member used to detect a dose amount may be the same as described above for detecting an event or it may be a different member. Alternatively the electronic label may be adapted to only detect dose amounts.

The housing may have a curved exterior portion, and the flexible sheet and the display may be mounted at least in part to the curved exterior and/or interior portion of the housing. For example, the drug delivery device may have a pen configuration with a general round or oval form, the flexible sheet being applied to the housing as an exterior "label", e.g. by adhesive. Depending on the design of the input means the housing may be designed with openings allowing the input means to be actuated by internal mechanical elements, or portions of the flexible sheets comprising input means may be threaded through such openings and attached to an interior surface of the housing. Further input means may be arranged in the interior of the drug delivery device and adapted to cooperate with input means of the flexible sheet.

To cost-effectively provide a "label-like" electronic assembly one or more or all of the detection means, display, processor, and energy source may be in the form of printed electronics.

In a further aspect of the invention a flexible sheet with electronics as described above is provided, the sheet being adapted to be mounted on a drug delivery device of the type described above.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Other specific drugs could be growth hormone and drugs for the treatment of haemophilia and inflammation.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

Figure 1A:
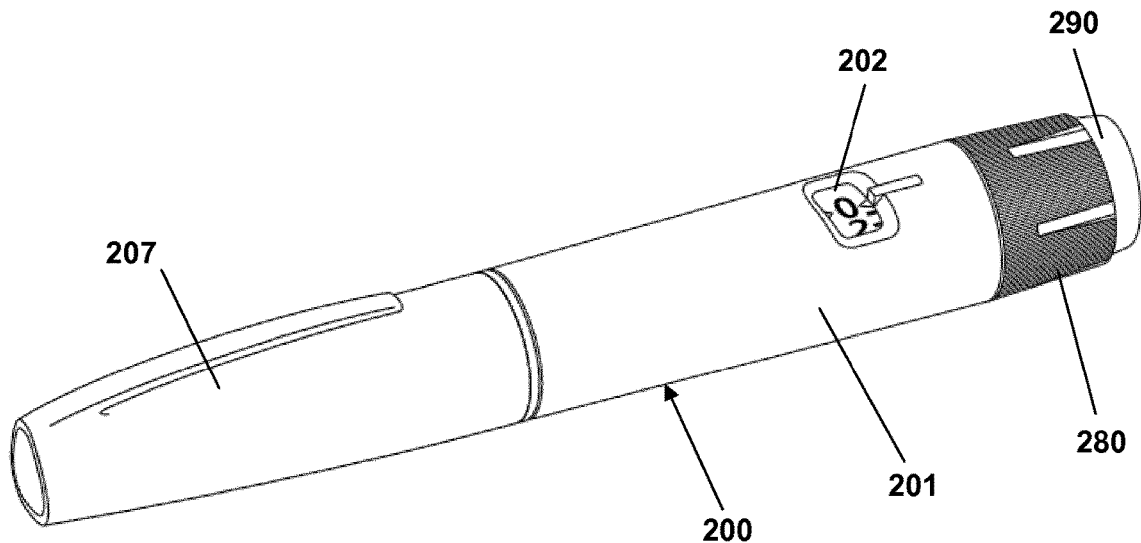
FIG. 1A shows a drug delivery pen device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessary can be assembled to provide a unitary or functional assembly during a given assembly procedure but is merely used to describe components grouped together as being functionally more closely related.

Before turning to embodiments of the present invention per se, an example of a pre-filled drug delivery will be described, such a device providing the basis for the exemplary embodiments of the present invention. Although the pen-formed drug delivery device 200 shown in FIG. 1 may represent a "generic" drug delivery device, the actually shown device is a FlexTouch® pre-filled drug delivery pen as manufactured and sold by Novo Nordisk A/S, Bagsværd, Denmark.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 280 serves to manually set a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
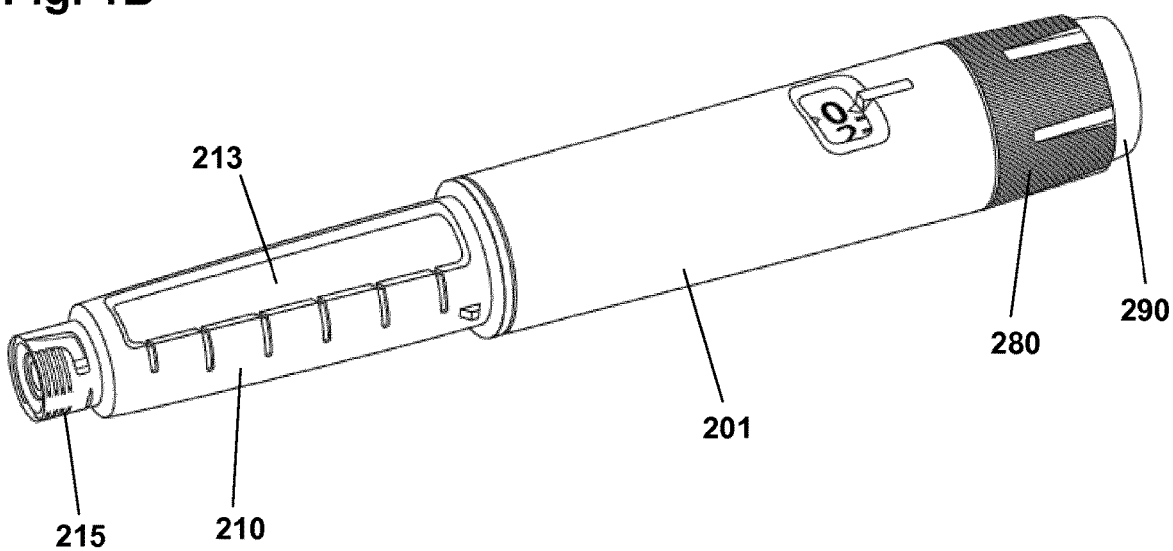
FIG. 1B shows the pen device of FIG. 1A with the pen cap removed.

Although FIG. 1 shows a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to electronic circuitry adapted to be incorporated in and interact with a drug delivery device, an exemplary embodiment of such a device will be described for better understanding of the invention.

Figure 2:
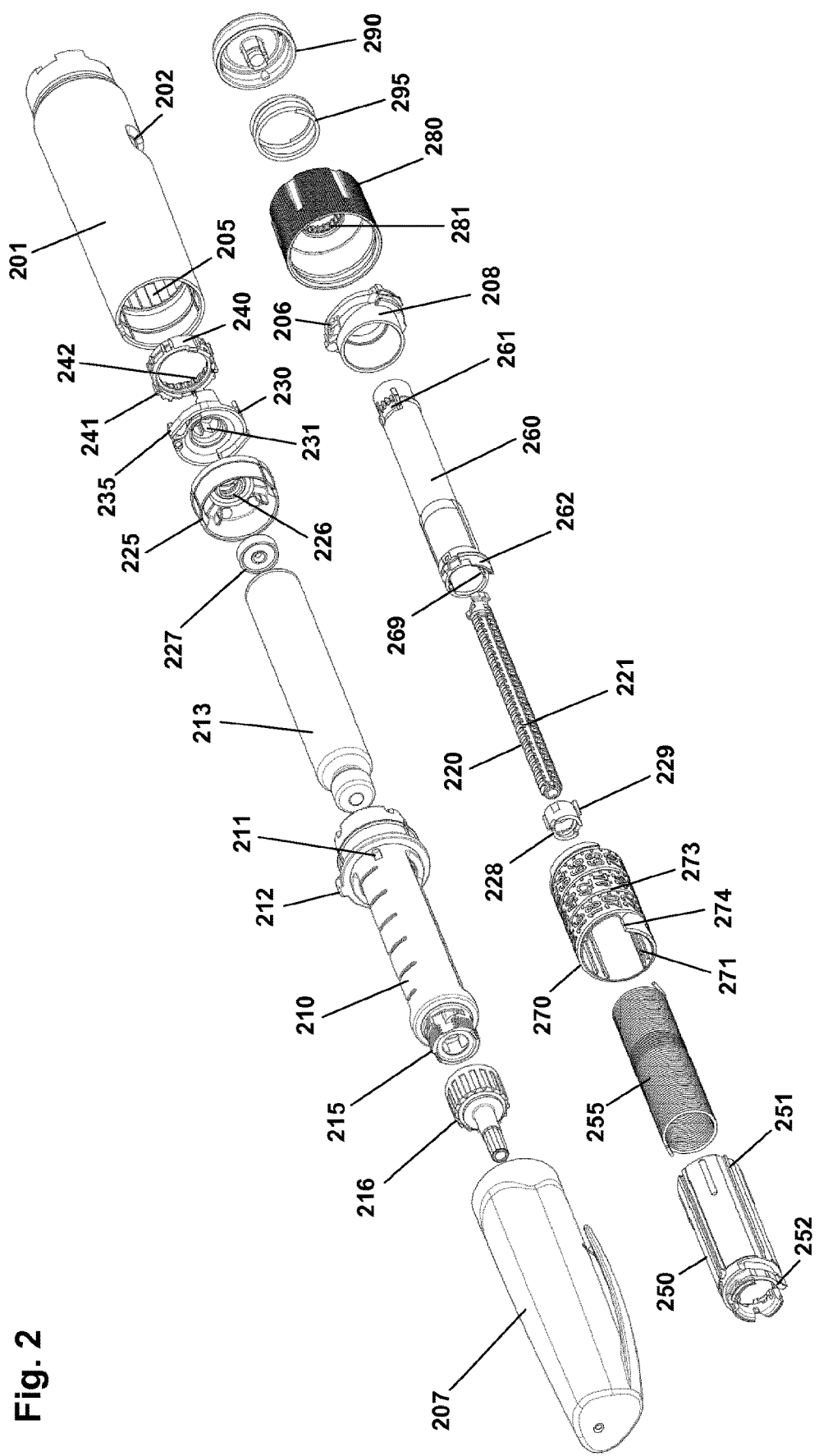
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 200 shown in FIG. 1. More specifically, the pen comprises a tubular housing 201 with a window opening 202 and onto which a cartridge holder 210 is fixedly mounted, a drug-filled cartridge 213 being arranged in the cartridge holder. The cartridge holder is provided with distal coupling means 215 allowing a needle assembly 216 to be releasable mounted, proximal coupling means in the form of two opposed protrusions 211 allowing a cap 207 to be releasable mounted covering the cartridge holder and a mounted needle assembly, as well as a protrusion 212 preventing the pen from rolling on e.g. a table top. In the housing distal end a nut element 225 is fixedly mounted, the nut element comprising a central threaded bore 226, and in the housing proximal end a spring base member 208 with a central opening is fixedly mounted. A drive system comprises a threaded piston rod 220 having two opposed longitudinal grooves 221 and being received in the nut element threaded bore, a ring-formed piston rod drive element 230 rotationally arranged in the housing, and a ring-formed clutch element 240 which is in rotational engagement with the drive element (see below), the engagement allowing axial movement of the clutch element. The clutch element is provided with outer spline elements 241 adapted to engage corresponding splines 204 (see FIG. 8B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 231 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 235 adapted to engage corresponding ratchet teeth 205 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 228 is threadedly mounted and on the distal end a washer 227 is rotationally mounted. The EOC member comprises a pair of opposed radial projections 229 for engagement with the reset tube (see below).

The dial system comprises a ratchet tube 250, a reset tube 260, a scale drum 270 with an outer helically arranged row of dose numerals, a user-operated dial member 280 for setting a dose of drug to be expelled, a release button 290 and a torque spring 255 (see FIG. 3). The reset tube is mounted axially locked inside the ratchet tube but is allowed to rotate a few degrees (see below). The reset tube comprises on its inner surface two opposed longitudinal grooves 269 adapted to engage the radial projections 229 of the EOC member, whereby the EOC can be rotated by the reset tube but is allowed to move axially. The clutch element is mounted axially locked on the outer distal end portion of the ratchet tube 250, this providing that the ratchet tube can be moved axially in and out of rotational engagement with the housing via the clutch element. The dial member 280 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 290 is axially locked to the reset tube but is free to rotate. A return spring 295 provides a proximally directed force on the button and the thereto mounted reset tube. The scale drum 270 is arranged in the circumferential space between the ratchet tube and the housing, the drum being rotationally locked to the ratchet tube via cooperating longitudinal splines 251, 271 and being in rotational threaded engagement with the inner surface of the housing via cooperating thread structures 203, 273, whereby the row of numerals passes the window opening 202 in the housing when the drum is rotated relative to the housing by the ratchet tube. The torque spring is arranged in the circumferential space between the ratchet tube and the reset tube and is at its proximal end secured to the spring base member 208 and at its distal end to the ratchet tube, whereby the spring is strained when the ratchet tube is rotated relative to the housing by rotation of the dial member. A ratchet mechanism with a flexible ratchet arm 252 is provided between the ratchet tube and the clutch element, the latter being provided with an inner circumferential teeth structures 242, each tooth providing a ratchet stop such that the ratchet tube is held in the position to which it is rotated by a user via the reset tube when a dose is set. In order to allow a set dose to be reduced a ratchet release mechanism 262 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
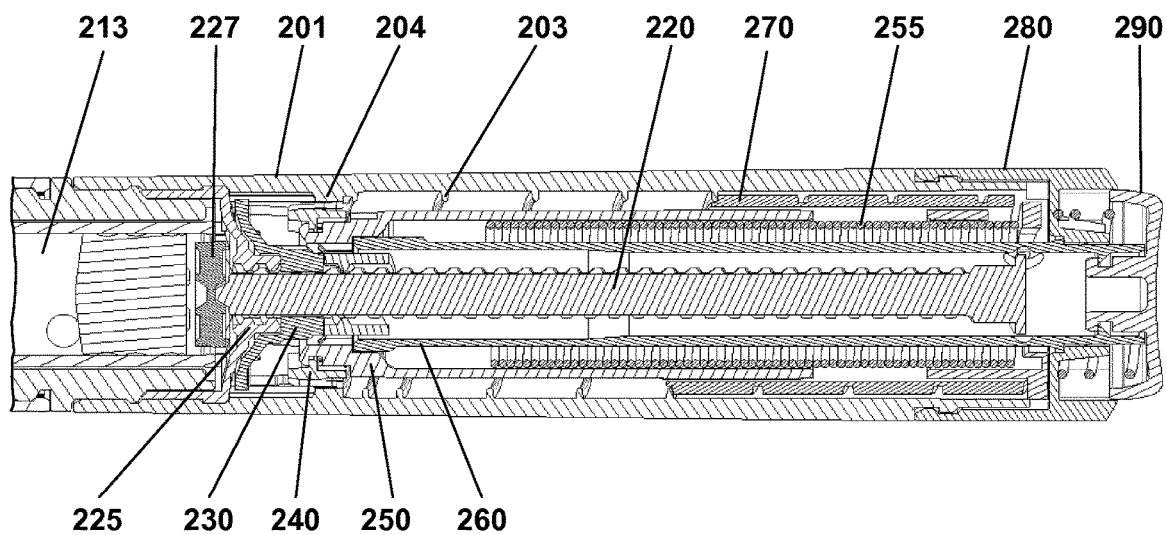

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 220, the actual displacement of the plunger being performed by the piston rod. During dose delivery, the piston rod is rotated by the drive element 230 and due to the threaded interaction with the nut element 225 which is fixed to the housing, the piston rod moves forward in the distal direction. Between the rubber piston and the piston rod, the piston washer 227 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 234 which prevent the drive element from rotating clockwise (seen from the push button end). Due to the engagement with the drive element, the piston rod can thus only move forwards. During dose delivery, the drive element rotates anti-clockwise and the ratchet arms 235 provide the user with small clicks due to the engagement with the ratchet teeth 205, e.g. one click per unit of insulin expelled.

Turning to the dial system, the dose is set and reset by turning the dial member 280. When turning the dial, the reset tube 260, the EOC member 228, the ratchet tube 250 and the scale drum 270 all turn with it. As the ratchet tube is connected to the distal end of the torque spring 255, the spring is loaded. During dose setting, the arm 252 of the ratchet performs a dial click for each unit dialled due to the interaction with the inner teeth structure 242 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 202.

The ratchet 252, 242 between the ratchet tube and the clutch element 240 prevents the spring from turning back the parts. During resetting, the reset tube moves the ratchet arm 252, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 242 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
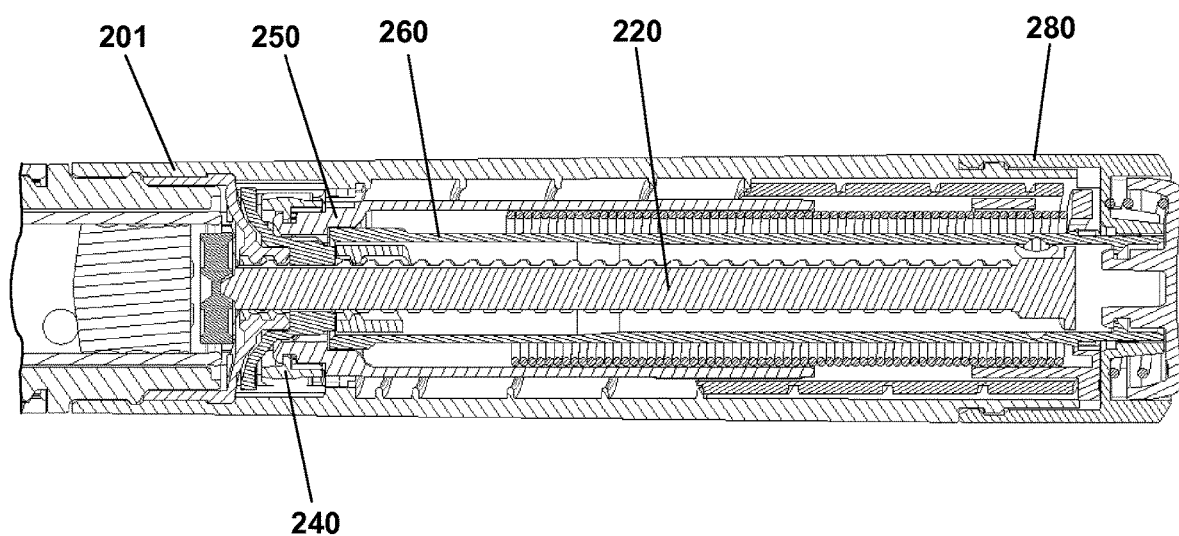

To deliver a set dose, the push button 290 is pushed in the distal direction by the user as shown in FIG. 3B. The reset tube 260 decouples from the dial member and subsequently the clutch element 240 disengages the housing splines 204. Now the dial mechanism returns to "zero" together with the drive element 230, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 228 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 270 is provided with a distal stop surface 274 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialling mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 206 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 281 engaging a number of corresponding teeth arranged on a flexible carrier portion 261 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, embodiments of the present invention will be described.

Figure 4:
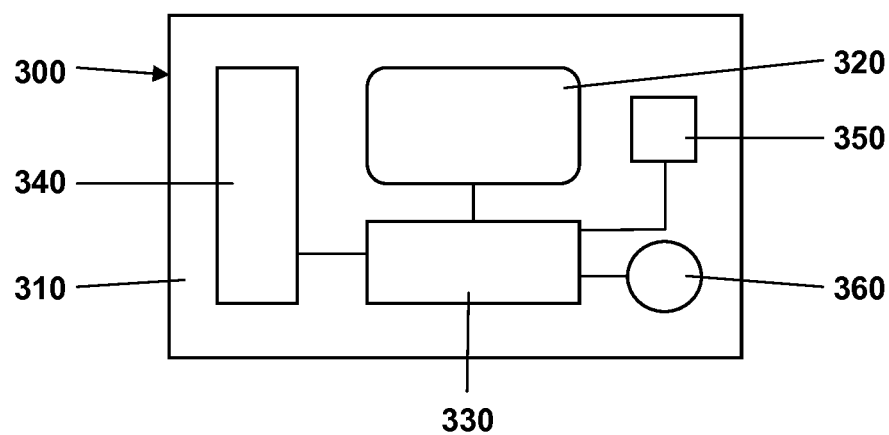
FIG. 4 shows a schematic representation of an "electronic label"

FIG. 4 shows a schematic representation of an "electronic label device" 300 in the form of a flexible sheet on which a number of structures are mounted or formed. The shown exemplary embodiment is adapted to be used with a modified version of the above-described pen-formed drug delivery device, the modifications providing a dose related output which can be captured by the circuitry of the label device.

More specifically, the label is formed from a polymeric flexible sheet substrate 310 and comprises a processor with associated memory, either a printed logic unit or a mounted chip 330 (or a combination of the two), at least one battery 340 which is either printed onto the substrate, laminated or mounted to it, input means 350 for capturing data from the drug delivery device onto which the label is mounted, and wireless communication means 360 allowing the label to communicate with an external device in order to transmit captured data. In the shown embodiment the label comprises a printed display 320 which may be adapted to display dose size and/or time related information to the user, however, this is an optional feature.

The input means may be in the form of a pair of electrical terminals adapted to cooperate with corresponding output terminals arranged on a surface portion of the drug delivery device. The output terminals are associated with an internal switch arrangement being actuated during use of the device. The switch arrangement may a be simple arrangement adapted to detect a single event, e.g. an end-of-dose state, or a more advanced arrangement providing an output indicative of the size of an expelled and/or set dose amount. Alternatively the input means may be in the form of sensor means per se. For example, the input means may be a magnetic sensor adapted to detect movement of a magnetic member in the drug delivery device, or the sensor may be an acoustic sensor adapted to detect a specific sound pattern generated during dose setting and/or dose expelling. Alternatively, the sensor may be in the form of a switch structure actuated by movement of a structure in or on the drug delivery device. As a further alternative the sensor may be in the form of a piezo sensor adapted to detect movement of a component or portion of the drug delivery device on which the label is mounted. A number of sensor/input arrangements are described in greater detail in WO 2015/071354 which is hereby incorporated by reference.

In order to minimize size, complexity and cost of an electronic label for a drug delivery device it would be desirable if as much structure as possible could be transferred to an external device. Indeed, it is always possible to reduce size, complexity and cost of a given device by eliminating structures and rely on external structures and resources.

Since many people today carry a so-called "smartphone" at practically all times, an obvious solution to the problems of providing processing power and a display would be to transmit the monitored data to a smartphone and use the processing power and the display of the smartphone. However, using traditional means of wireless communications, e.g. Bluetooth® and similar technologies, requires relatively much power and space-consuming electronics, all adding to volume and costs of the electronic label.

Addressing this issue, the present inventors have realized that a technical solution to this problem would be to use sound or ultrasound as means of communication. The use of sound signals to transmit data is well known, e.g. wireless remote controllers for TV sets typically used ultrasound in the seventies, but sound is not used much in modern data transfer technologies, due to the limited data transfer rate. However, for the suggested use, only a very small amount of data needs to be transferred, which makes sound or ultrasound useable.

Correspondingly, in an aspect of the present invention, the communication means is in the form of a sound transducer working in the near-ultrasound/ultrasound frequency range, e.g. 15-25 kHz (traditionally ultrasound is defined as frequencies above 20 kHz).

The background for this choice of communication means is based on the realization that a typical smartphone, e.g. a telephone device running either an iOS or an Android operating system, is provided with a built-in speaker and microphone which can be used through an app to communicate with the label device of the present invention. In this way data transferred from the label device to the smartphone and smartphone app, can be processed, stored and displayed on the smartphone. In this way the label device does not have to be provided with a display. The data stored on the smartphone can then be transmitted to a database by the smartphones internet connection, if required or desired.

Ultrasound is defined as sound at frequencies above what can be heard by the human ear, e.g. 20 kHz as mentioned above. Although smartphone speakers and microphones are not designed specifically for use with ultrasound, experiments have shown that the speakers and microphones of the most popular smartphones are capable of transmitting and receiving data through their speakers and microphones at near-ultrasound or low ultrasound frequencies, i.e. 18-21 kHz. At frequencies between 18-20 KHz some people, especially young people will be able to hear a very high pitched sound during communication, but communication just above 20 KHz should be hearable to only very few people.

Figure 5A:
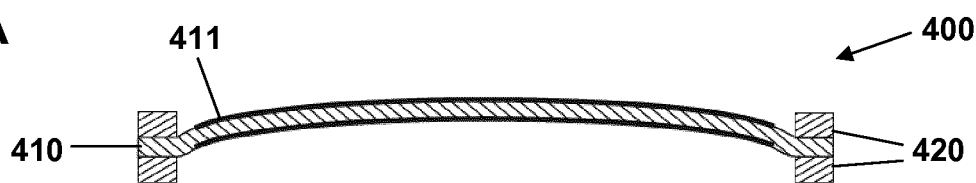
FIGS. 5A-5D illustrates the concept of a piezoelectric sound emitter.
Figure 5B:
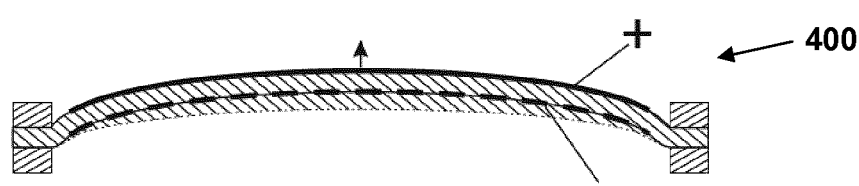
Figure 5C:
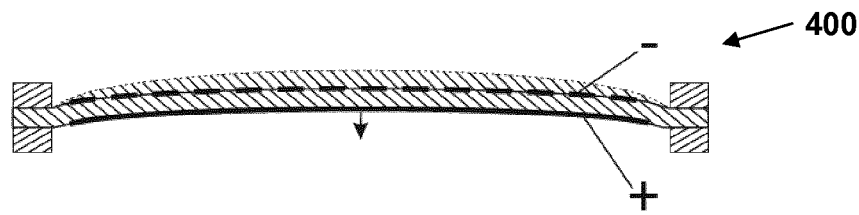
Figure 5D:
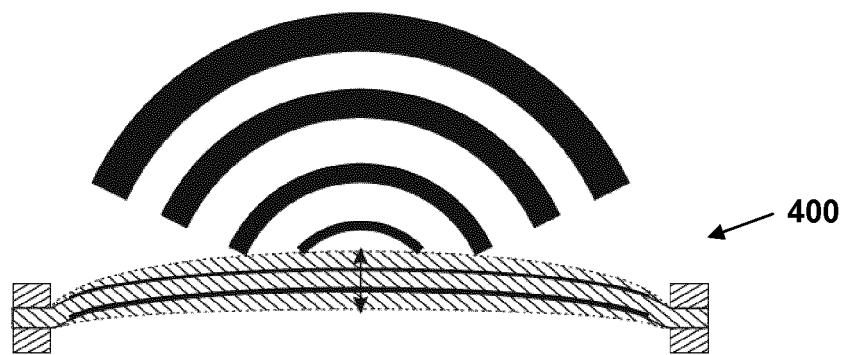

With reference to FIGS. 5A-5D the basic principle of a piezoelectric speaker will be described. More specifically, FIG. 5A shows a piezoelectric sound emitter 400 in the form of a polyvinylidene fluoride (PVDF) foil 410 portion which is provided with conductive layers on each side and held in place between two clamping members 420, this providing a membrane 411 adapted to move in a controlled way. When a voltage is applied across the foil, the foil stretches and warps and pushes the air in front of the foil as shown in FIG. 5B. When the voltage is reversed on the foil, the foil contracts and pulls the air in front of the foil as shown in FIG. 5C. When an alternating signal is applied to the foil, the foil induces vibrations and thus sound in the air as illustrated in FIG. 5D. For the PVDF piezo speaker to work properly it is required that the moving part of the film can either move freely or is attached to a member that can be caused to vibrate by the tension applied to it by the foil. It is also required that the foil is firmly fixed along the edge of the moving portion of the foil to cause the foil to warp when stretched.

In FIG. 4 a schematic representation of an electronic label device comprising a carrier foil on which a number of components and structures are mounted or formed is shown. When making labels containing e.g. current-generating cells ("batteries") and displays, especially when manufactured using printed electronics, these components become sensitive in some degree to changes in air humidity. For example, too dry air dries out the electronic ink in a printed display. This can have the effect that the display stops working in the sense that the displayed values or symbols cannot be changed. If air humidity becomes too high the label and the incorporated components, e.g. printed features such as a batteries and displays will absorb moisture. If for example a display becomes too moist, the required update interval for the display is decreased and the necessary power to change or maintain the display appearance increases significantly. This can have the effect that the battery runs flat prior than expected or that expected lifetime of battery (and thus device) is decreased significantly. Correspondingly, too high air humidity may lead to the battery electrolyte absorbing moisture leading to increased self-discharging and accelerated decay.

Addressing this issue, the solution to the problem has been to seal the label in a watertight foil material. In respect of the term "watertight" this is in most cases a relative term as most materials to a certain degree are permeable to water depending on e.g. the material thickness. Thus the term watertight in the present context indicates that a give structure is "sufficiently watertight" for the intended purpose, e.g. to allow a given product to be used and handled by a consumer in an everyday setting and exposed to normal moisture conditions.

Figure 6A:
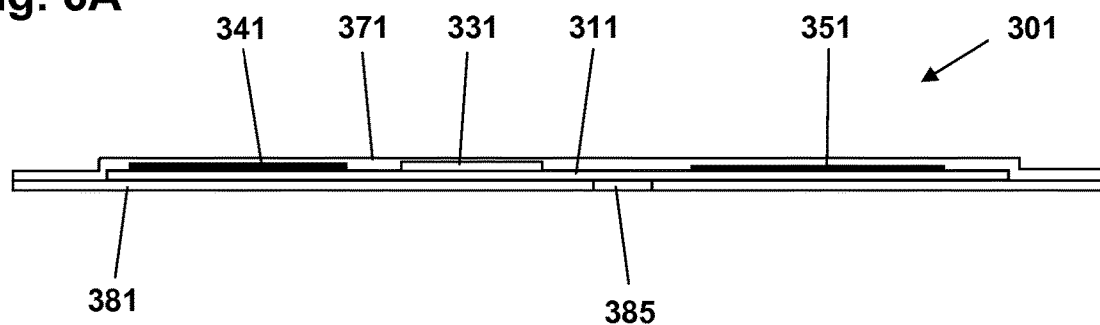
FIGS. 6A-6D show cross-sectional views of electronic labels.

More specifically, FIG. 6A shows schematically a cross-section through an electronic label 301 of the general type shown in FIG. 4, the label comprising a carrier foil 311 on which is formed or mounted a number of components, e.g. a printed battery 341, a mounted processor 331 and a printed display 351. The carrier foil is selected and optimized for allowing the described printing and mounting of components and may be in the form of a PVDF as described above. A sound transducer structure is not shown (see FIGS. 7A and 7B below). The label device 301 comprises an upper sealing foil 371 and a lower sealing foil 381 bonded circumferentially to each other as well as to the upper respectively lower surface of the carrier foil. In the shown embodiment a contact structure 385 is embedded in the lower foil layer to allow electric communication with switch structures housed in the device on which the label device is mounted. Examples of label devices laminated between layers of protective foil members are shown in e.g. U.S. Pat. No. 8,384,517 and US 2016/0263327.

Figure 6B:
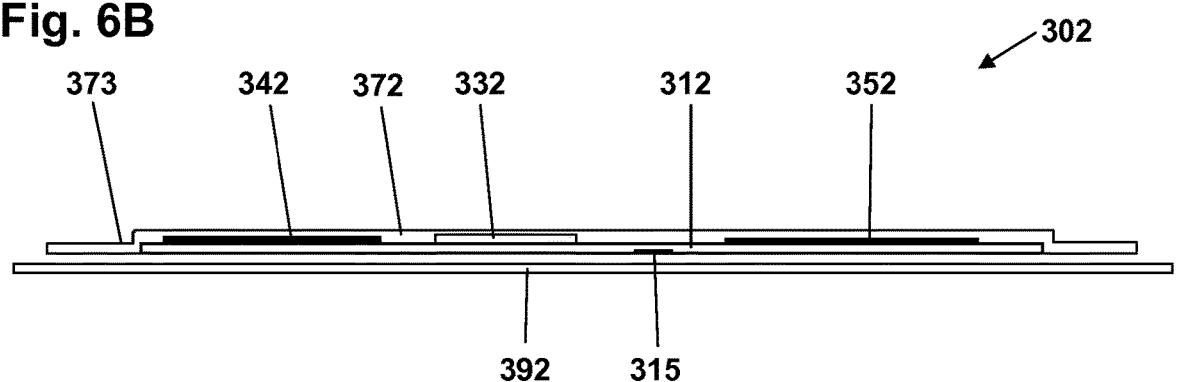

FIG. 6B shows schematically a cross-section through an alternative design for an electronic label 302 of the general type shown in FIG. 4, the label comprising a carrier foil 312 on which is formed or mounted a number of components, e.g. a printed battery 342, a mounted processor 332 and a printed display 352. A sound transducer structure is not shown (see FIGS. 7A and 7B below). The carrier foil is selected and optimized for allowing the described printing and mounting of components and may be in the form of a piezoelectric PVDF as described above. The label device 302 comprises an upper sealing foil 372 bonded to the upper surface of the carrier foil and providing a circumferential free edge portion. In the shown embodiment a contact structure 386 is provided on the lower surface of the carrier foil to allow electric communication with switch structures housed in the device on which the label device is mounted. Thus, in contrast to the label device 301 described with reference to FIG. 6A the label device 302 of FIG. 6B does not comprise a lower sealing foil. In this way the label device can be manufactured more cost-effectively just as the omission of a layer provides a label device which is thinner and more flexible and thus more suitable for mounting on a curved surface such as on the exterior of a pen-formed drug delivery device. The lower surface of the label device may be provided with an adhesive layer and a thereto attached peelable temporary backing foil 392 which can be removed (as shown) just prior to mounting of the label device on a drug delivery device. Such a temporary backing foil could also serve as a moisture barrier during storage of the label device.

The deletion of the lower sealing foil is based on the realization that the label device per se is not an independently working device but can more correctly be considered a component of a device assembly, the two components in combination providing the desired functionality. Correspondingly, the functionality of the deleted lower sealing foil is provided by the structure on which the label device is mounted, e.g. the portion of the drug delivery device housing the label device is intended to be mounted on. As indicated above, most materials are not 100% water impermeable. Correspondingly, the housing portion on which the label device is to be mounted should be manufactured from a polymeric material and having a thickness ensuring the desired low level of water permeability. Alternatively, the housing portion may be coated with a layer of material providing the desired level of water permeability.

Besides the benefit of lower production costs of the label and increased flexibility, compared to sealing both sides of the label, using the device housing material as a moisture barrier on the adhesive/bonding side of the label also makes any contacting simpler. If contacting between device and label are necessary, this will present a challenge if the label is sealed on both sides. Then the sealing foil would have to be penetrated and connection established between the inside of the label laminate and the surface of the device. When using the device housing as a seal, connection points can be moulded into the device housing and sealed and all contacting connections between label and device are thereby made within the sealed volume and not in the sealing interface.

Figure 6C:
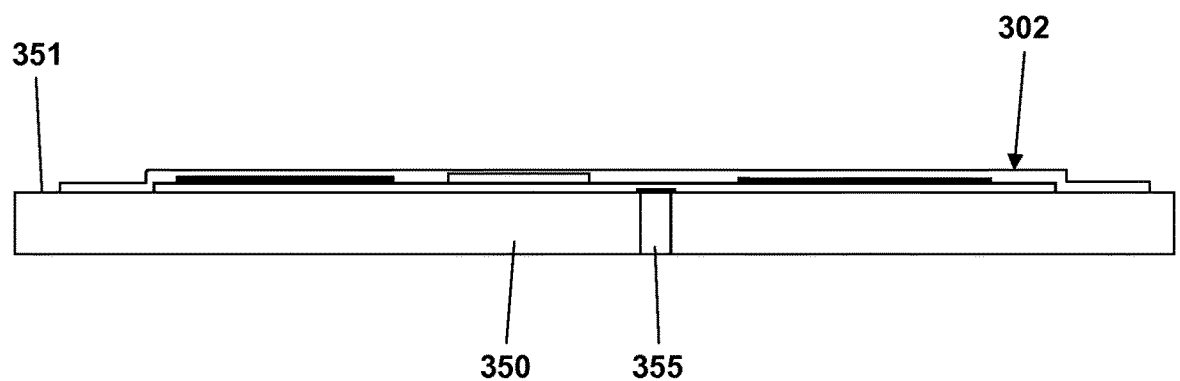

FIG. 6C shows schematically the label device 302 of FIG. 6B mounted on the outer surface 351 of a pen-formed drug delivery device (see also FIG. 8), the housing wall 350 providing the lower/inner moisture sealing for label device. This design also allows the label contact structure 315 to be arranged in direct contact with the corresponding contact structure 355 on the pen device. For example, the housing and the carrier foil may comprise corresponding galvanic contact terminals 355, 315 arranged operationally connected to each other. In an alternative embodiment the contact structures may be in the form of a piezoelectric sensor 315 and a deflectable housing portion, e.g. as will be described below with reference to FIGS. 8A and 8B.

As described with reference to FIGS. 6B and 6C a number of components are formed or mounted on an upper surface of a flexible carrier foil after which a sealing foil is applied to cover and seal the components, whereby the components are laminated between the two layers.

Figure 6D:

FIG. 6D shows an alternative design for an electronic label 303 in which a number of components 333, 343, 353 are formed or mounted on a lower surface of a flexible laminate foil 370 comprising a lower carrier foil 313 and an upper sealing foil 373. As appears, after the components are formed or mounted on the lower surface of the laminate foil they are not protected inside the laminate as in the above-described embodiment of FIGS. 6B and 6C, however, an adhesive layer applied to the lower surface of the label device together with a removable protective sheet as shown in FIG. 6B could be used to protect the components until the label is mounted on a housing 353. Although it may appear more efficient to form or mount the components directly on a laminate foil, the upper sealing foil may alternatively be attached to the carrier foil in a subsequent process step.

In FIG. 6D the components are for illustrative purposes shown as relatively thick structures, however, at least the printed components can be expected to be relatively thin structures. Whereas in the FIG. 6B embodiment relatively thick components would bulge outwards, in the FIG. 6D embodiment such components would bulge inwards. Correspondingly, an outer housing surface on which the label is to be mounted may be provided with (shallow) cavities accommodating such bulging components. In case one of the components is a display it follows that both layers of the laminate layers would have to possess transparent properties.

For the above-described embodiments an electronic label device is provided for mounting on a housing surface, the label device comprising a laminate with a lower carrier foil and an upper sealing foil, the components being arranged on the upper or lower surface of the carrier foil. Alternatively a number of components may formed or mounted on an upper or lower surface of a flexible carrier foil which can be mounted on a housing surface, an upper sealing foil being applied subsequently.

In a further alternative embodiment the carrier foil may be replaced with a carrier coating applied to a sealing foil, the carrier coating allowing the components to be formed or mounted onto the coated surface of a single-layer sealing foil.

An example of a manufacturing and mounting process for an electronic label device (comprising two sealing layers) is described in greater detail in WO 2015/071354.

Figure 7A:
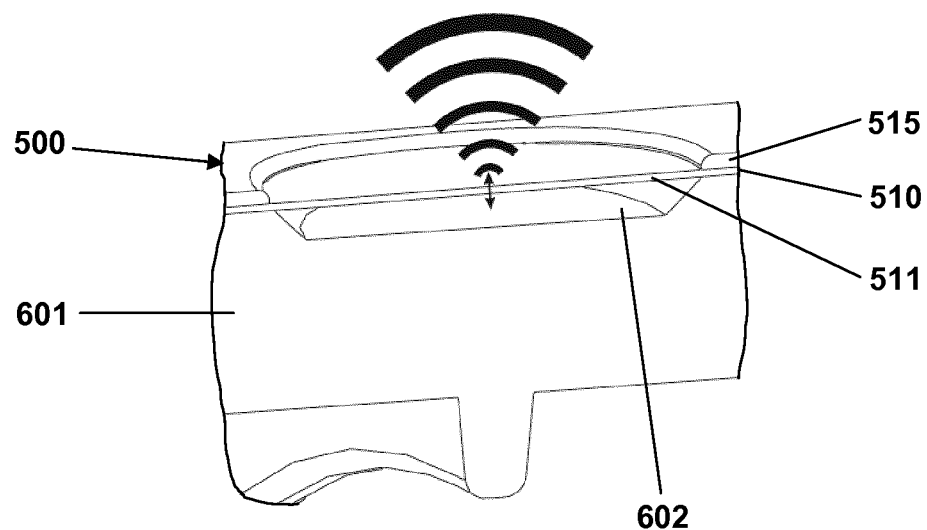
FIGS. 7A and 7B show embodiments of a piezoelectric sound emitter mounted on a drug delivery device housing portion.

In a first application embodiment the foil is suspended over a cavity in a device housing to enable free motion of the sound emitting portion of the PVDF-based label for transmission of data using sound or ultrasound. More specifically, FIG. 7A illustrates a portion of an electronic label device 500 comprising a flexible piezoelectric foil 510 serving as a substrate for forming or mounting the above-described components of the label device (not shown), on top of which is laminated a protective layer 515, the protective layer comprising an opening thereby forming the integrated speaker/microphone 511 for sonic data transmission, i.e. a bidirectional sound transducer. In the shown embodiment the label is fixed to a device housing 601 with an adhesive, but the moving transducer portion of the foil is allowed to move freely, the edges being clamped between the protective layer and the device housing. The section of the label intended to emit and receive sound is prevented from adhering to the device housing by introducing a cavity 602 in the device housing.

Figure 7B:
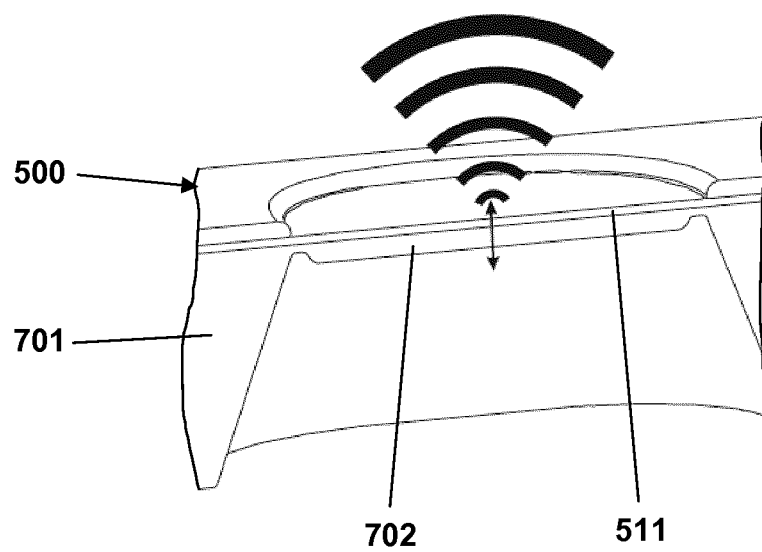

In a second application embodiment, a section of the device housing is partly disconnected from the rest of the housing to form a membrane 702 which remains connected to the housing structure 701 only through a few weakened and flexible connections. This allows the section of the housing to perform small movements relative to the housing and act as a speaker/microphone membrane. In this embodiment the foil acts as a driver actuating the moveable section of the housing structure. FIG. 7B shows a portion of the label device 500 with a build-in speaker/microphone for sonic data transmission. In this application embodiment the label is fixed to the device housing with an adhesive, both at the main portion of the housing and the moveable membrane portion of the housing. The section of housing allowed to perform limited motion acts as a membrane/membrane stiffener and makes the foil less vulnerable to puncture or damage. However, it also increases the moving mass significantly as well as the dampening and will limit both frequency generation and response. In the shown application embodiments the label device is the same, however, alternatively the label may be optimized for the specific application.

As described above, an electronic label can be formed from a polymeric flexible sheet substrate provided with a processor and associated memory, a battery, input means for capturing data from the drug delivery device onto which the label is mounted, wireless communication means allowing the label to communicate with an external device in order to transmit captured data, as well as conducting structures allowing the different components to communicate. Optionally a display may also be provided. One or more of the mentioned structures may be provided in the form of printed electronics (electronics circuits made by layers of conductive ink printed on a foil), whereas others may be surface-mounted directly on the flexible sheet.

For such a label device the piezoelectric foil used to create a combined speaker/microphone as described above may also form a flexible sheet substrate if coated with an isolating layer, this allowing the additional components and structures to be formed or mounted on the piezoelectric foil. Indeed, the portion of the foil providing the sound transducer does not have to be coated. Connections to the conductive layers on each side of the piezoelectric foil may be established by leaving connection points uncoated by the isolating layer. In this way a combined speaker and microphone can be added to an electronic label device at a very small additional cost.

In the above examples a combined speaker/microphone transducer has been described, however, in alternative embodiments two individual piezoelectric transducers could be used, this allowing each transducer to be optimized for the specific purpose. In addition, the input means may be in the form of a piezoelectric acoustic sensor adapted to detect a specific sound pattern generated during dose setting and/or dose expelling. Further, more than one transducer may be provided for a given purpose, e.g. allowing sound to be emitted in different directions.

Regardless of the actual design of the speaker/microphone transducer system, the label device and smartphone needs to be aware of the presence of each other in order to be able to communicate. Since one of the reasons for using sound as means of communication is the limited access to power in the label device, the system should be designed to reduce the power consumption of the device to a minimum. One option is to let the device listen for communication requests from a smartphone if transmission of sound requires significantly more power than listening in the device in question. However, since the device will be "first to know" if new data is available, it may result in a lower power consumption to let the device transmit a request for communication with the smartphone. That way data exchange can be performed and the device can stop requesting communication when data has been transmitted and not send out new request until device has been used again. Thus the number of requests and data transfers can be reduced to only what is necessary. If data transfer is requested by the smartphone there is a risk of wasting battery power in the device on either numerous transfers of the same last data or numerous messages from the device that there are no new data to transmit.

After having described exemplary embodiments of the invention a drug delivery device in which the above-described pairing concept could be implemented will be described.

Figure 8A:
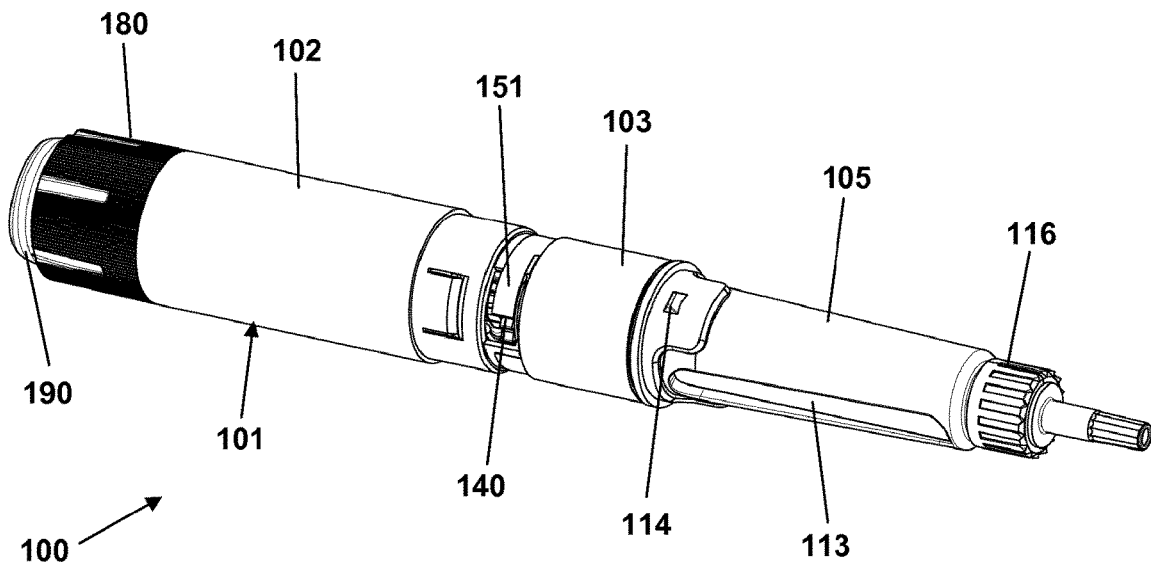
FIG. 8A shows a further drug delivery device.
Figure 8B:
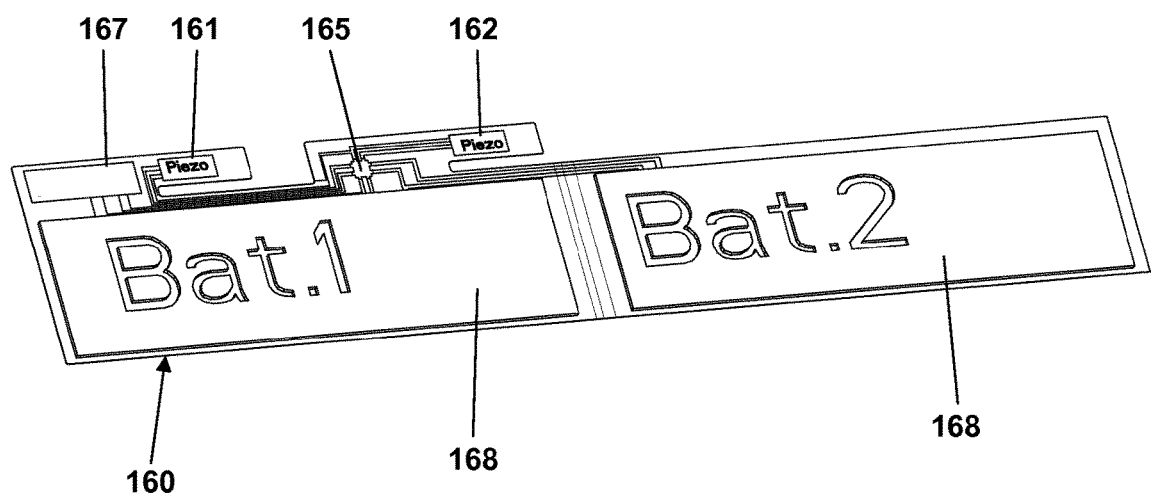
FIG. 8B shows an electronic label in the form of flexible sheet with electronic circuitry.

The pen device 100 in FIG. 8A comprises a proximal body or drive assembly portion with a housing 101 in which a drug expelling mechanism is arranged or integrated, and a distal cartridge holder portion 105 in which a drug-filled transparent cartridge 113 with a distal needle-penetrable septum is arranged and retained in place by a non-removable cartridge holder 105 attached to the proximal portion. The cartridge holder 105 comprises openings allowing a portion of the cartridge to be inspected, distal coupling means allowing a needle assembly 116 to be releasably mounted as well as proximal coupling means in the form of two opposed protrusions 114 allowing a cap (not shown) to be releasably mounted covering the cartridge holder 105. In the shown embodiment the housing comprises a proximal housing portion 102 and a distal housing portion 103 which in a fully assembled state of the pen device is fixedly connected to each other via an intermediate tubular housing portion (not shown) covering the shown flexible arm 150 (see below), thereby forming a unitary housing. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug and which can then be expelled when the button 190 is actuated. The expelling mechanism comprises a helically rotatable scale drum member with a plurality of indicia in the form of dose size numerals printed thereon, the dose size number corresponding to the currently set dose size being shown in a display opening (not seen in FIG. 8A). Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button may be arranged to move proximally during dose setting corresponding to the set dose size, and then to be moved distally by the user to expel the set dose, e.g. as in a FlexPen® manufactured and sold by Novo Nordisk A/S.

Although FIG. 8A shows a drug delivery device of the prefilled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

The expelling mechanism incorporated in pen device 100 comprises a ring-formed piston rod drive element and an actuator member 140 in the form of a rotatable component that rotates together with the piston rod drive element during expelling of a dose of drug, the actuator member 140 thereby experiencing unidirectional rotational movement relative to an indicator structure fixedly disposed within the housing 101. In the shown embodiment the indicator structure is in the form of a pair of opposed circumferentially arranged deflectable flexible arms 151 each engaging the actuator member.

The actuator member 140 is in the form of a toothed wheel having a plurality of axially oriented ridges protruding radially outwards and being spaced circumferentially and equidistantly. Each ridge is formed with a gradually rising leading side and a sharply dropping trailing side. In the shown embodiment 24 ridges are spaced with angular steps of 15 degrees. Between any two neighbouring ridges a groove is formed.

Each of the deflectable arms 151 includes at its free end a tip portion with a radially inwards pointing first surface which is angled to be generally parallel with a gradually rising side of a ridge. Each tip portion further has a second opposed surface which is angled to be generally parallel with the sharply dropping side of a ridge. The radially inwards pointing first surface of the tip portions is configured to ride over consecutive ridges as the actuator member 140 rotates relative to the deflectable arms so that the tip portions of the first and second deflectable arm remain in intimate contact with the outer contour of the actuator member 140 as the latter rotates. The free end of a flexible arm 151 is biased slightly inwards when the tip portion is seated in a groove, the biasing force increasing when the free end of the arm is lifted outwards by the ridge formations as the actuator member rotates.

In the shown embodiment, the tip portions of the deflectable arms are located approximately 178 degrees apart so that, as the actuator member 140 rotates, the first deflectable arm will experience cooperation with a particular first ridge slightly before the second deflectable arm will experience cooperation with a ridge arranged diametrically opposite from the first protrusion. This arrangement is described in greater detail in EP application 17205309 hereby incorporated by reference. Alternatively, a single arm design may be used.

Figure 9:
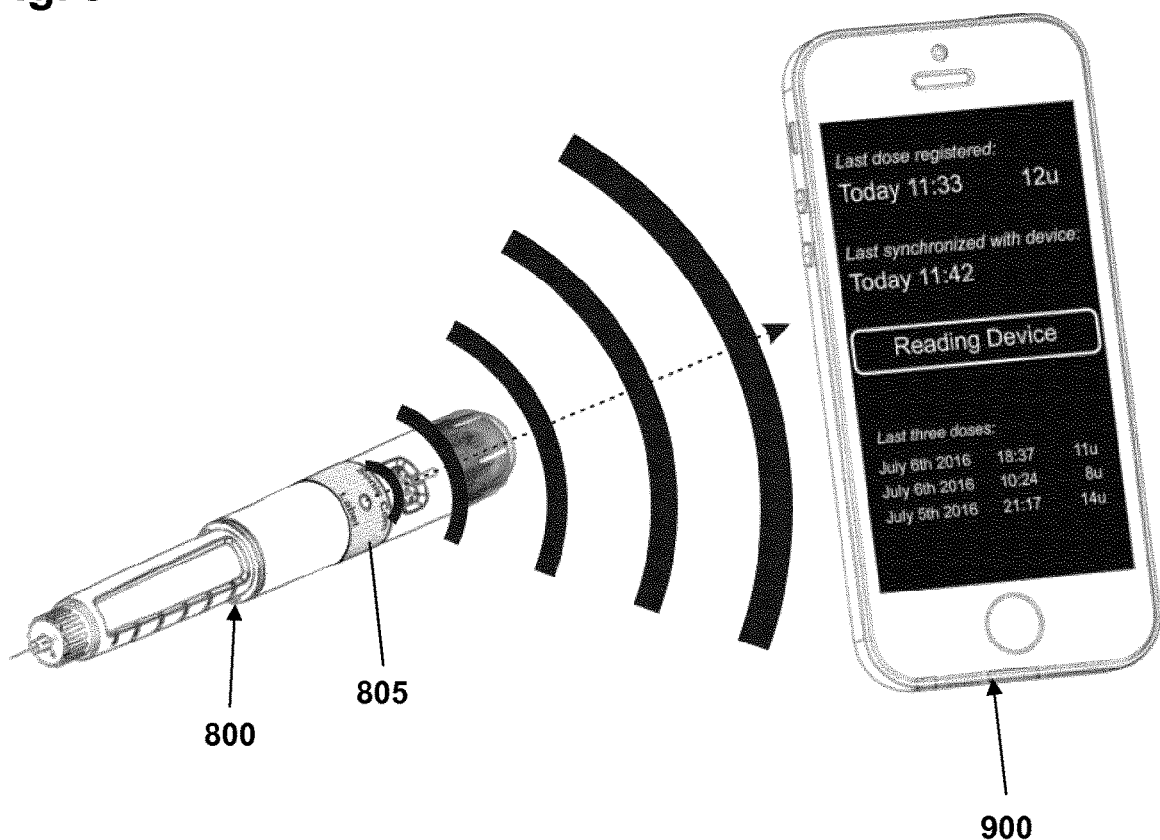
FIG. 9 shows an assembly comprising a pen device provided with an electronic label and an external display device, the two devices communicating using sound transmission.

In order to monitor operation of the device by electronic means, corresponding electronic circuitry 160 is adapted to be disposed on the device 100 for registering events associated with operations performed by the device, i.e. expelling of a set dose of drug. In FIG. 9 a corresponding pen device with a circumferentially arranged electronic label is shown. In the shown embodiment of FIG. 8B the electronic circuitry 160 is in the form of a flexible sheet on which is formed and mounted input means adapted to be actuated, directly or indirectly, by movement of the indicator structure(s), a processor and memory 165, wireless communication means in the form of a sound transducer 167, and an energy source 168, wherein the processor is adapted to determine on the basis of measured values from the input means a rotational position and/or a rotational movement of the actuator member 140 to thereby calculate the size of an expelled dose of drug. The flexible sheet is adapted to be mounted on housing parts of the pen device by e.g. adhesive means, the nature of the flexible sheet allowing it to be mounted also on curved surfaces.

In the shown embodiment the input means is active transducers in the form of piezoelectric sensors 161, 162 adapted to be mounted onto the flexible arms 151 and thereby generating an output as the flexible arms are moved by the rotating actuator member 140. Although not incorporated in the shown embodiment, the electronic circuitry may in other embodiments further include a display so as to offer a visible read-out of information related to registered events. In the shown embodiment energy is provided by two electric cells 168.

One or more of the above-described components may be printed onto the flexible sheet, e.g. the piezoelectric sensors, the sound transducer, a display, the antenna and the energy source. Other components, e.g. the processor and associated memory may be surface mounted on the flexible sheet.

FIG. 9 shows a drug delivery device 800 on which is mounted an electronic label device 805, which in the shown embodiment comprises no display, the two devices forming a combined drug delivery device adapted to generate and register events related to expelling an amount of drug from the drug delivery device. In the shown embodiment for each expelling event a data set is generated comprising data indicative of the amount of drug expelled in combination with a relative time stamp, the generated data set being communicated to an external device in form of a smartphone 900. A typical use scenario implementing two-way communication could thus comprise the following steps.

After data related to a dosing event has been captured by the label device, e.g. an end-of-dose signal, the label device starts for a pre-determined amount of time or a pre-determined number of times to request connection to a previously paired smartphone for transfer of data be emitting request signal via the speaker. If no connection with a smartphone is established the label device will end transmission and store the data in its memory for subsequent transmission together with the next set of data.

When the smartphone is within range and the "label app" is either open or running in the background on the smartphone listening for data transfer requests, the smartphone will register the communication request from the label device via the smartphone microphone and transmit an ID verification code and ask the label device to transmit data.

When the label device receives verification of the smartphone ID and the data transfer request via the label device microphone, the label device starts transmitting data to the smartphone via the label device speaker to the smartphone microphone. During data transfer the app may indicate on the smartphone display that data transfer is in progress.

When data transfer is complete the smartphone verifies completion of communication to the label device, which will not transmit communication requests until new dose event data has been captured. On the smartphone, once data has been received and processed, it can be displayed and stored by the app. The data can also subsequently be relayed to a cloud storage for e.g. sharing with the user's GP, for generating statistical data, or for creating graphic presentations of user history on other platforms, e.g. a user's PC.

In an alternative simplified set up data is transmitted using a transmit-only protocol, a full or partial log being transmitted at the end of each dosing event.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device, comprising:
   a housing having an exterior surface,
   a drug-filled cartridge or structure for receiving a drug-filled cartridge, the cartridge comprising an outlet and an axially displaceable piston,
   drug expelling structure comprising:
      a drive member adapted to engage and axially move the piston to thereby expel an amount of drug from the cartridge through the outlet, and
      an indicator member arranged to move corresponding to an action performed on or by the drug delivery device,
   electronic circuitry comprising:
      sensor structure adapted to detect movement of the indicator member,
      wireless communication structure,
      a processor adapted to (i) receive input from the sensor structure indicative of indicator member movement and (ii) control the wireless communication structure to transmit a data signal comprising coded information derived from received input from the sensor structure, and
      an energy source,
   wherein the wireless communication structure is in the form of a sound transducer, and
   wherein the delivery device further comprises a flexible carrier foil on which is formed or mounted:
      the energy source,
      the sound transducer, and
      the processor,
   wherein the flexible carrier foil is mounted on the exterior surface of the housing, and the flexible carrier foil is a piezoelectric foil, a portion of the piezoelectric foil forming the sound transducer.

2. The drug delivery device as in claim 1, wherein the sound transducer is:
   (i) a sound emitter, or
   (ii) a bidirectional sound transducer, the processor being adapted to receive input from the sound transducer.

3. The drug delivery device as in claim 1, wherein the sound transducer emits sound signals in the 15-25 kHz range.

4. The drug delivery device as in claim 1, wherein the sound transducer is a piezoelectric sound transducer.

5. The drug delivery device as in claim 1, wherein the housing exterior surface comprises a cavity over which at least a portion of a piezoelectric foil is arranged.

6. The drug delivery device as in claim 1, wherein the housing comprises a portion with reduced wall thickness over which at least a portion of the sound transducer is arranged.

7. The drug delivery device as in claim 1, wherein:
   the drug expelling structure further comprises a dose setting member allowing a user to set a dose amount of drug to be expelled, and
   the indicator element is adapted to move during setting and/or expelling of a dose amount, the amount of movement being indicative of a size of the set and/or expelled dose amount.

8. An electronic label adapted to be mounted on an exterior surface of a drug delivery device housing, a drug delivery device comprising:
   the drug delivery device housing having an exterior surface,
   a drug-filled cartridge or structure for receiving a drug-filled cartridge, the cartridge comprising an outlet and an axially displaceable piston,
   drug expelling structure comprising:
      a drive member adapted to engage and axially move the piston to thereby expel an amount of drug from the cartridge through the outlet, and
      an indicator member arranged to move corresponding to an action performed on or by the drug delivery device,
   wherein the electronic label comprises a flexible carrier foil comprising a piezoelectric foil on which is formed or mounted:
      an energy source,
      a sound transducer comprising a piezoelectric sound transducer, and
      a processor adapted to (i) receive input from the drug delivery device indicative of indicator member movement, and (ii) control the sound transducer to emit a coded signal comprising information derived from received input from the drug delivery device indicative of indicator member movement,
   wherein a portion of the piezoelectric foil forming the sound transducer.

9. The electronic label as in claim 8, wherein the sound transducer is:
   a sound emitter, or
   a bidirectional sound transducer, the processor being adapted to receive input from the sound transducer.

10. The electronic label as in claim 8, wherein the sound transducer emits sound signals in the 15-25 kHz range.

11. The electronic label as in claim 8, further comprising sensor structure adapted to detect, directly or indirectly, movement of the indicator member, the processor being adapted to receive input from the sensor structure.

* * * * *